US00PP33695P2

(12) United States Plant Patent
van den Hoogen

(10) Patent No.: US PP33,695 P2
(45) Date of Patent: Nov. 23, 2021

(54) ***HYPERICUM* PLANT NAMED 'ALLHYKIM'**

(50) Latin Name: *Hypericum hybrida*
Varietal Denomination: Allhykim

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 0 days.

(21) Appl. No.: 16/974,077

(22) Filed: Sep. 22, 2020

(51) Int. Cl.
*A01H 5/08* (2018.01)
*A01H 6/00* (2018.01)

(52) U.S. Cl.
USPC ..... Plt./442

(58) Field of Classification Search
USPC ..... Plt./442, 226
CPC ... A01H 5/08; A01H 5/02; A01H 5/00; A01H 6/00; A01H 5/04
See application file for complete search history.

(56) References Cited

PUBLICATIONS

Florius Flowers Our Hypericum Coco, retrieved on Mar. 29, 2021, retrieved from the Internet at https://floriusflowers.com/hypericum-coco-series/, 4 pp. (Year: 2021).*
Youtube New! Hypericum Coco Kimono—Florius Flower May 1, 2020, retrieved from the Internet at https://www.youtube.com/watch?v=87LI-4ILK9g, 2 pp. (Year: 2020).*

* cited by examiner

*Primary Examiner* — June Hwu
(74) *Attorney, Agent, or Firm* — C. Anne Whealy

(57) ABSTRACT

A new and distinct cultivar of *Hypericum* plant named 'Allhykim', characterized by its upright plant habit; vigorous growth habit; dark green-colored leaves; freely flowering habit and high fruit density; large glossy bright salmon pink-colored fruits; and suitability as a cut flower plant.

2 Drawing Sheets

Botanical designation: *Hypericum hybrida.*
Cultivar denomination: 'ALLHYKIM'.

BACKGROUND OF THE INVENTION

The present invention relates to a new and distinct cultivar of *Hypericum* plant, botanically known as *Hypericum hybrida*, typically grown as cut flower and hereinafter referred to by the name 'Allhykim'.

The new *Hypericum* plant is a product of a planned breeding program conducted by the Inventor in Cuijk, The Netherlands. The objective of the breeding program is to create new *Hypericum* plants with numerous attractive glossy fruits.

The new *Hypericum* plant originated from an open-pollination in August, 2013 in Cuijk, The Netherlands of a proprietary selection of *Hypericum hybrida* identified as code number 2-2013-58, not patented, as the female, or seed parent with an unknown selection of *Hypericum hybrida* as the male, or pollen, parent. The new *Hypericum* plant was discovered and selected by the Inventor as a single flowering plant from within the progeny of the stated open-pollination in a controlled outdoor nursery environment in Cuijk, The Netherlands in September, 2013.

Asexual reproduction of the new *Hypericum* plant by vegetative cuttings in a controlled outdoor nursery environment in Cuijk, The Netherlands since September, 2013 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allhykim'. These characteristics in combination distinguish 'Allhykim' as a new and distinct *Hypericum* plant:

1. Upright plant habit.
2. Vigorous growth habit.
3. Dark green-colored leaves.
4. Freely flowering habit and high fruit density.
5. Large glossy bright salmon pink-colored fruits.
6. Suitable as a cut flower plant.

Plants of the new *Hypericum* differ primarily from plants of the female parent selection in fruit color as plants of the new *Hypericum* have bright salmon pink-colored fruits whereas fruits of plants of the female parent selection are pink in color.

Plants of the new *Hypericum* can be compared to plants of the *Hypericum hybrida* 'Allloco', not patented. In side-by-side comparisons plants of the new *Hypericum* differ primarily from plants of 'Allloco' in the following characteristics:

1. Plants of the new *Hypericum* and 'Allloco' differ in fruit color as plants of the new *Hypericum* have salmon pink-colored fruits whereas fruits of plants of 'Allloco' are light pink in color.

2. Fruits of plants of the new *Hypericum* are not as glossy as fruits of plants of 'Allloco'.
3. Sepals of plants of the new *Hypericum* are larger than sepals of plants of 'Allloco'.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph on the first sheet is a side perspective view of a fruiting stem of 'Allhykim'.

The photograph on the second sheet comprise close views of the lower surface of a typical leaf, the upper surface of a typical leaf, and lateral and terminal views of typical developing fruits with and without sepals of 'Allhykim'.

DETAILED BOTANICAL DESCRIPTION

Plants used for the aforementioned photographs and following description were grown in September in a ground bed in an outdoor nursery in Cuijk, The Netherlands and under cultural practices typical of commercial *Hypericum* production. During the production of the plants, day temperatures ranged from 13° C. to 26° C. and night temperatures ranged from 6° C. to 16° C. Plants were one year old when the photographs and description were taken. In the following description, color references are made to The Royal Horticultural Society Colour Chart, 2015 Edition, except where general terms of ordinary dictionary significance are used.

Botanical classification: *Hypericum hybrida* 'Allhykim'.

Parentage:

*Female, or seed, parent*.—Proprietary selection of *Hypericum hybrida* identified as code number 2-2013-58, not patented.

*Male, or pollen, parent*.—Unknown selection of *Hypericum hybrida*, not patented.

Propagation:

*Type cutting*.—Vegetative cuttings.

*Time to initiate roots, summer*.—About 10 to 14 days at temperatures ranging from 12° C. to 30° C.

*Time to produce a rooted young plant, summer*.—About 24 to 32 days at temperatures ranging from 12° C. to 30° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Perennial shrub; upright plant habit; overall plant shape, narrow inverted triangle; vigorous growth habit and moderate to high growth rate.

*Branching habit*.—About three basal branches with numerous lateral branches develop per plant.

*Plant height*.—About 74.5 cm.

*Plant width* (*spread*).—About 18.6 cm.

*Lateral branch description*.—Length: About 56 cm. Diameter: About 5 mm. Internode length: About 5.8 cm. Strength: Moderately strong to strong. Texture and luster: Smooth, glabrous; glossy. Color, developing: Close to between 145C and 154C strongly flushed with close to 181B. Color, fully developed: Close to N199B to N199D.

Leaf description:

*Arrangement*.—Opposite, simple; sessile; about 20 leaves (ten pairs) per lateral branch.

*Length*.—About 6.8 cm.

*Width*.—About 4.9 cm.

*Shape*.—Ovate.

*Apex*.—Obtuse to shallowly emarginate.

*Base*.—Cordate.

*Margin*.—Entire.

*Texture and luster, upper surface*.—Slightly rugose; glabrous; slightly glossy.

*Texture and luster, lower surface*.—Slightly rugose; glabrous; matte.

*Venation pattern*.—Pinnate.

*Color*.—Developing leaves, upper surface: Close to 138A. Developing leaves, lower surface: Close to 138B. Fully expanded leaves, upper surface: Darker than N189A; venation, close to 144A. Fully expanded leaves, lower surface: Close to 191A to 191B, venation, close to 144C.

Flower description:

*Flower type, arrangement and flowering habit*.—Single rotate flowers arranged in terminal and axillary compound cymes; freely flowering habit with about 19 flowers per cyme; flowers face mostly upright.

*Fragrance*.—None detected.

*Natural flowering season*.—Plants flower continuously from mid-June to early September in The Netherlands; plants begin flowering about ten months after planting.

*Flower longevity*.—Flowers last about three days on the plant; flowers not persistent.

*Fruit longevity* (*postproduction*).—About 30 days.

*Flower buds*.—Length: About 9 mm. Diameter: About 6 mm. Shape: Broadly ovate. Color: Close to 12A.

*Inflorescence height*.—About 12.3 cm.

*Inflorescence diameter*.—About 11.4 cm.

*Flower diameter*.—About 2.8 cm.

*Flower depth* (*height*).—About 1.8 cm.

*Petals*.—Quantity and arrangement: Five in a single whorl. Length: About 1.3 cm. Width: About 9 mm. Shape: Ovate to broadly elliptic, concave; horizontal to slightly reflexed. Apex: Acute, unequal. Base: Attenuate. Margin: Entire. Texture and luster, upper surface: Smooth, glabrous; slightly glossy. Texture and luster, lower surface: Smooth, glabrous; glossy. Color: When opening and fully opened, upper surface: Close to 12A to 12B; color becoming closer to 13A with development. When opening and fully opened, lower surface: Close to 12A; color becoming closer to 13A with development.

*Sepals*.—Quantity and arrangement: Five in a single whorl. Length: About 1.1 cm. Width: About 8 mm. Shape: Broadly ovate; horizontal to moderately reflexed. Apex: Obtuse. Base: Truncate. Margin: Entire. Texture and luster, upper and lower surfaces: Smooth, glabrous; matte. Color: When opening, upper surface: Close to 138A. When opening, lower surface: Close to 183B. Fully opened, upper surface:

Darker than N189A. Fully opened, lower surface: Close to between 138A and 191A.

*Peduncles*.—Length: About 7.2 cm. Diameter: About 2 mm. Texture: Smooth, glabrous. Strength: Moderately strong. Aspect: Main peduncles, erect; lateral peduncles, about 40° from main peduncles axis. Color: Close to 146D strongly tinged with close to 182A.

*Pedicels*.—Length: About 1.6 cm. Diameter: About 1.75 mm. Texture: Smooth, glabrous. Strength: Moderately strong. Aspect: Main pedicels, erect; lateral pedicels, about 35° from main peduncles axis. Color: Close to 144A to 144B; proximally, tinged with close to 182A.

*Reproductive organs*.—Stamens: Quantity per flower: About 80. Filament length: About 1.3 mm. Filament color: Close to 12A. Anther length: About 0.5 mm. Anther shape: Broadly oval; dorsifixed. Anther color: Close to 14B. Pollen amount: Scarce. Pollen color: Close to 11A. Pistils: Quantity per flower: Single pistil with three stigmas. Pistil length: About 4 mm. Stigma shape: Club-shaped. Stigma color: Close to 33B. Style length: About 3 mm. Style color: Close to 12B. Ovary color: Close to 12B.

*Fruits*.—Quantity per lateral branch: About 19. Length: About 1.5 cm. Diameter: About 1.5 cm. Shape: Roughly spherical. Texture and luster: Smooth, glabrous; glossy. Color: Close to between 47C and 48A; towards the base, fading to close to 155A.

*Seeds*.—Quantity per fruit: About 100. Length: About 0.9 mm. Diameter: About 0.5 mm. Color: Close to 200A.

Pathogen & pest resistance: To date, plants of the new *Hypericum* have not been observed to be resistant to pathogens and pests common to *Hypericum* plants.

Temperature tolerance: Plants of the new *Hypericum* have been observed to tolerate high temperatures about 30° C. and to be hardy to USDA Hardiness Zone 7.

It is claimed:

1. A new and distinct *Hypericum* plant named 'Allhykim' as illustrated and described.

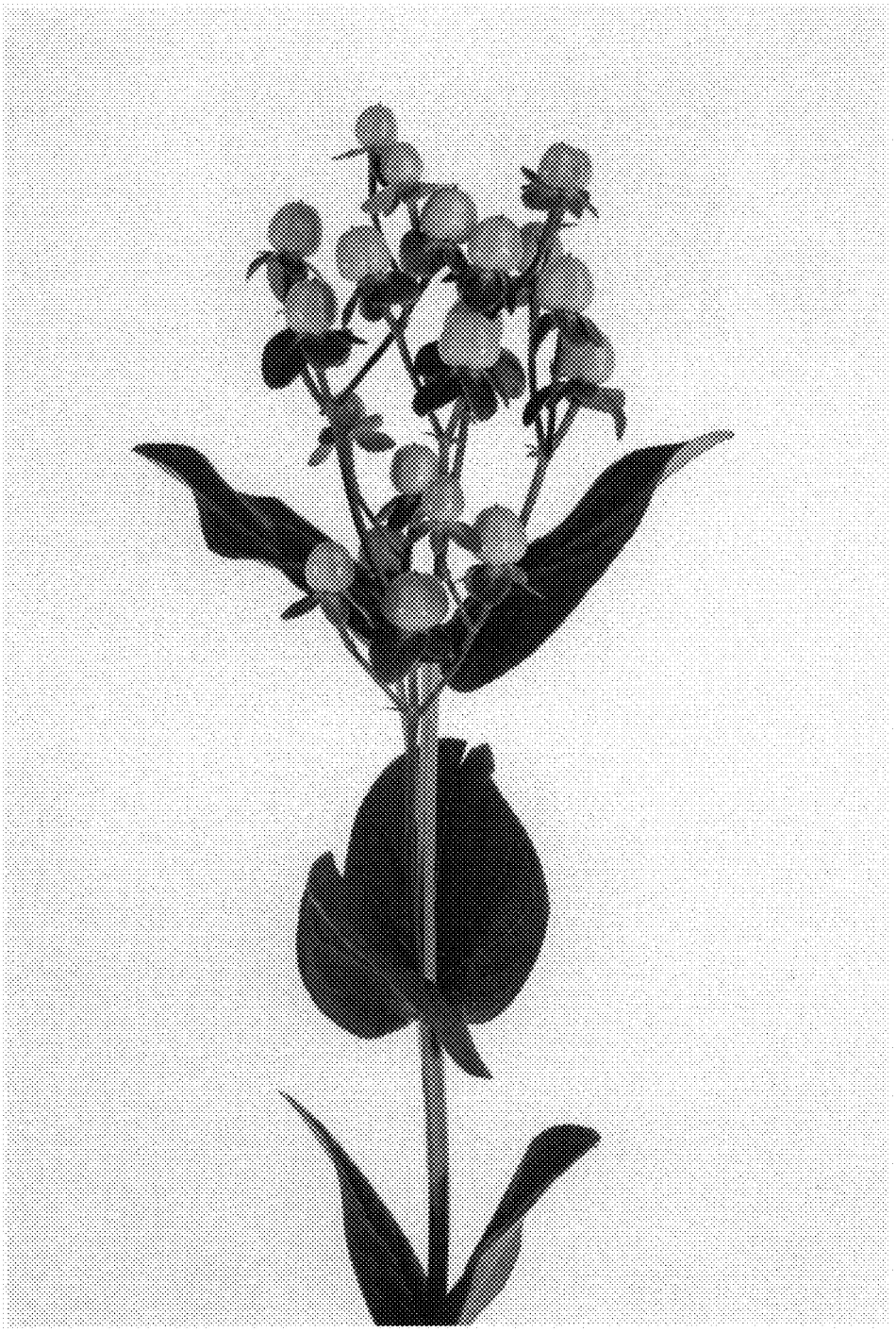

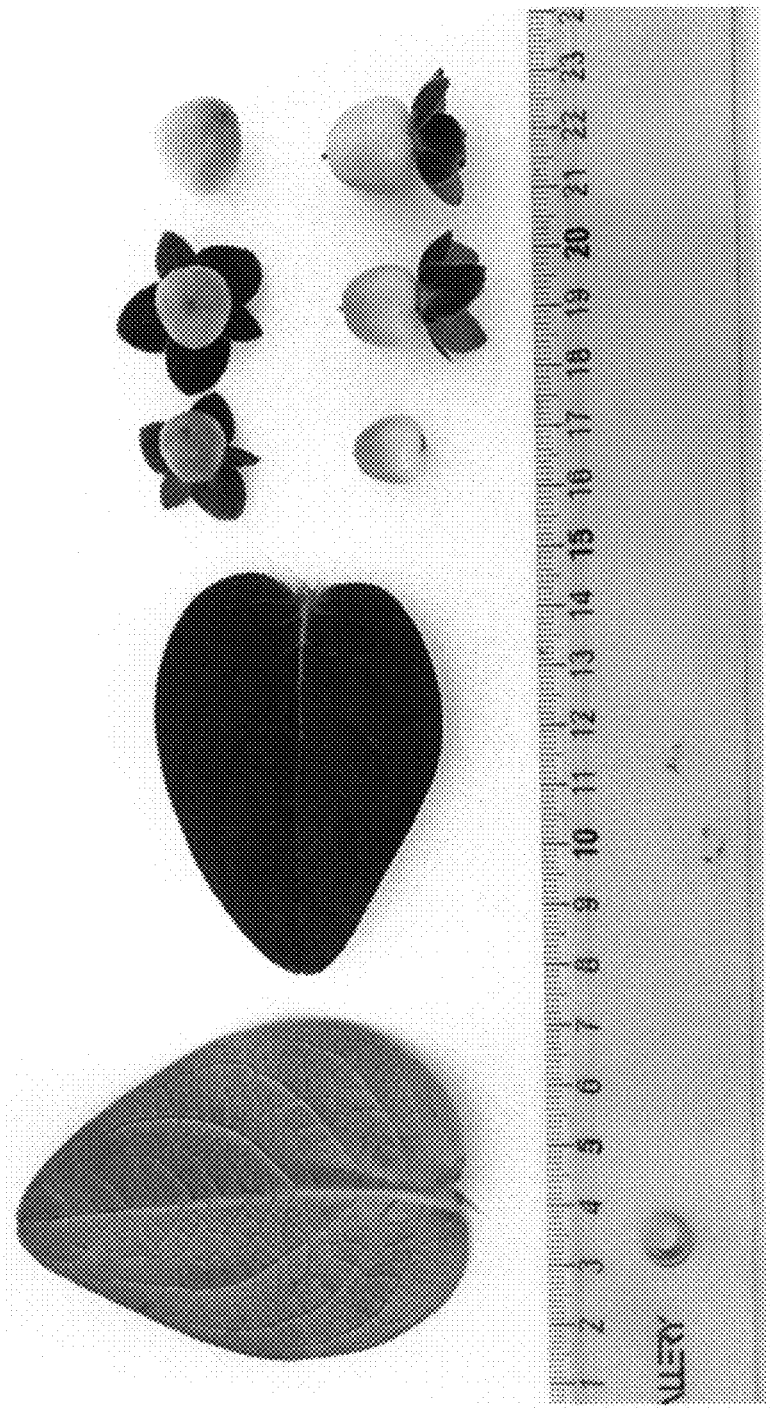

* * * * *